US 9,492,632 B2

(12) United States Patent
Limjaroen et al.

(10) Patent No.: US 9,492,632 B2
(45) Date of Patent: Nov. 15, 2016

(54) PACKAGING FOR A CATHETER

(75) Inventors: Paweena Limjaroen, Windsor, CA (US); Theodore Morris, Santa Rosa, CA (US); Amanda Kiefer, Memphis, TN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1277 days.

(21) Appl. No.: 13/086,164

(22) Filed: Apr. 13, 2011

(65) Prior Publication Data
US 2012/0261290 A1   Oct. 18, 2012

(51) Int. Cl.
*A61B 19/02* (2006.01)
*A61M 25/00* (2006.01)

(52) U.S. Cl.
CPC .................................. *A61M 25/002* (2013.01)

(58) Field of Classification Search
CPC .................................................. A61M 25/002
USPC ............. 206/571, 363–367, 476, 485, 362.4; 600/585, 434
See application file for complete search history.

(56) References Cited

U.S. PATENT DOCUMENTS

| | | | |
|---|---|---|---|
| 4,332,322 A * | 6/1982 | Jaeschke et al. | 206/364 |
| 4,496,045 A * | 1/1985 | Ferguson et al. | 206/63.3 |
| 5,344,011 A * | 9/1994 | DiBernardo et al. | 206/364 |
| 5,487,469 A * | 1/1996 | Roshdy et al. | 206/363 |
| 5,791,470 A * | 8/1998 | Usui | 206/362.4 |
| 6,871,740 B1 | 3/2005 | Cao | |
| 7,104,399 B2 | 9/2006 | Duffy et al. | |
| 7,234,597 B2 * | 6/2007 | Rowe et al. | 206/438 |
| 2004/0055919 A1 | 3/2004 | Rowe et al. | |
| 2004/0055926 A1 | 3/2004 | Duffy et al. | |
| 2005/0256501 A1 * | 11/2005 | Rispens | 206/364 |
| 2008/0006554 A1 | 1/2008 | Duffy et al. | |

FOREIGN PATENT DOCUMENTS

EP        0913164 A1    5/1999

* cited by examiner

*Primary Examiner* — Chun Cheung

(57) ABSTRACT

Packaging for a catheter includes coiled tubing for receiving the catheter and a mounting card coupled to the coiled tubing. The windings of the coiled tubing are welded together to maintain the coiled configuration. The mounting card includes an integral support flap for reducing the risk of damage during catheter insertion and removal, an integral luer retainer for securing a catheter luer, and one or more integral tabs for attaching catheter accessories to the packaging. The integral support flap creates a contact zone which discourages grasping the packaging at a location that can potentially damage an object passing through the packaging, such as a balloon and/or stent. The integral luer retainer is configured to selectively alternate between a configuration which secures the catheter luer and configuration which allows releases the luer for easy insertion and removal of the catheter.

13 Claims, 10 Drawing Sheets

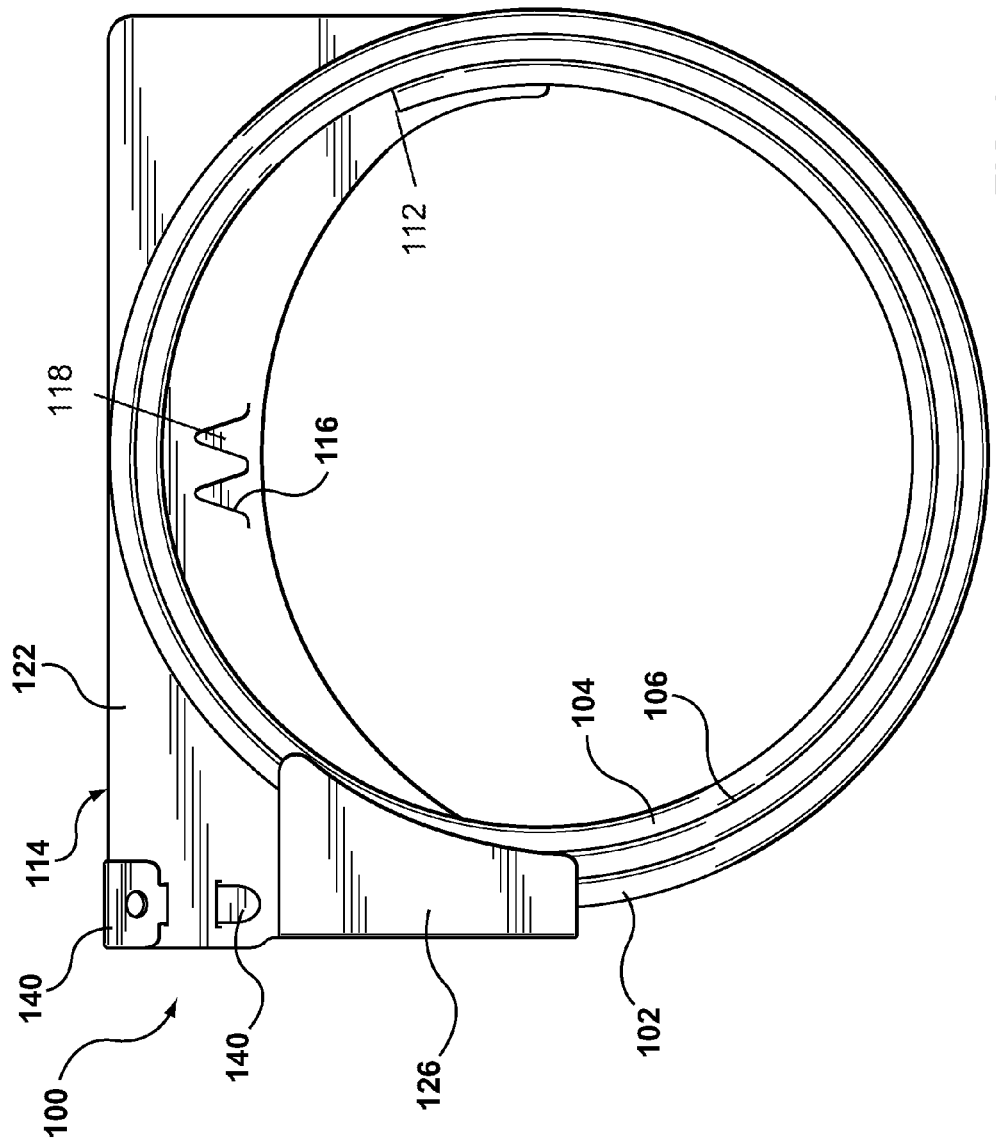

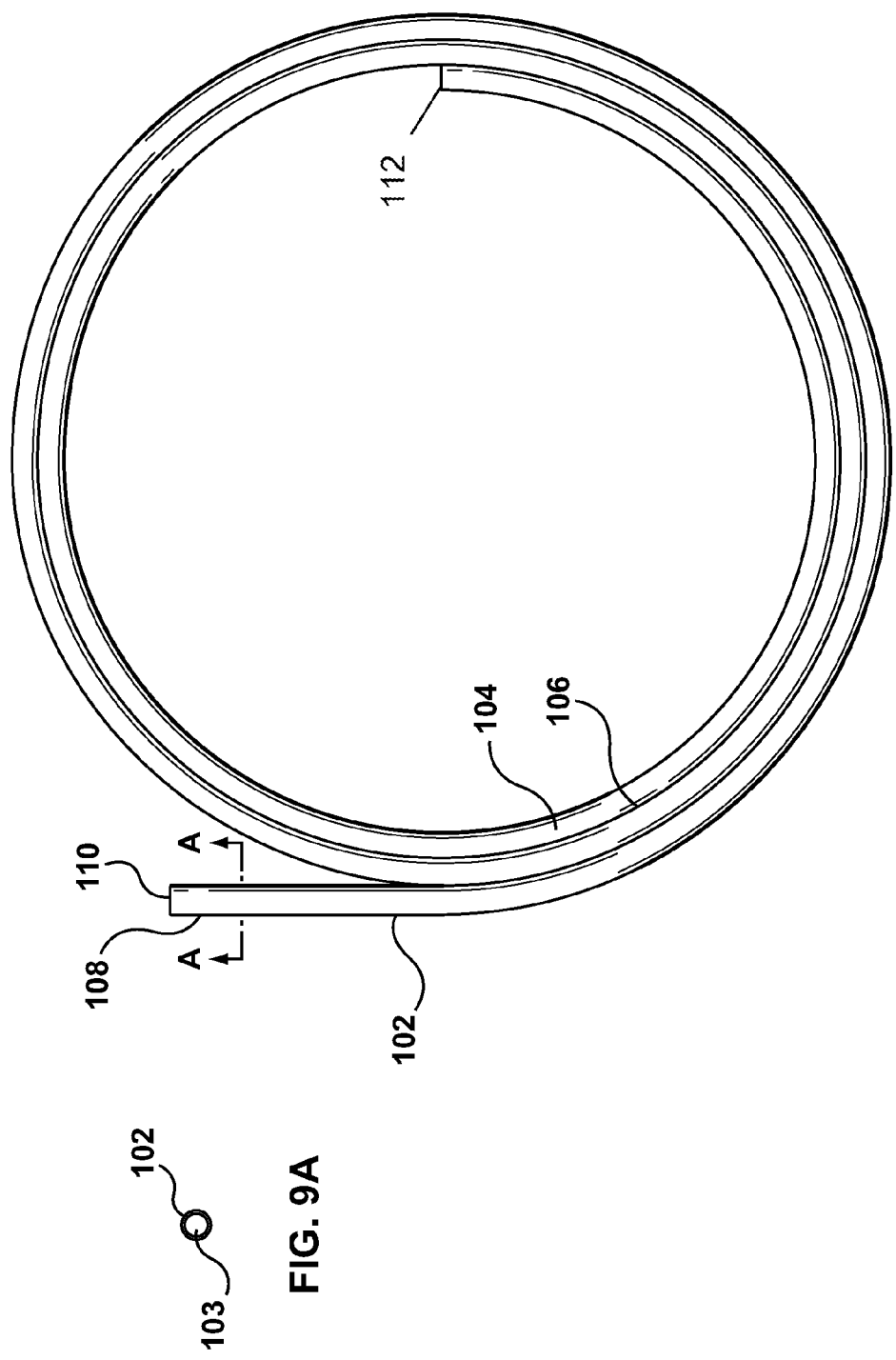

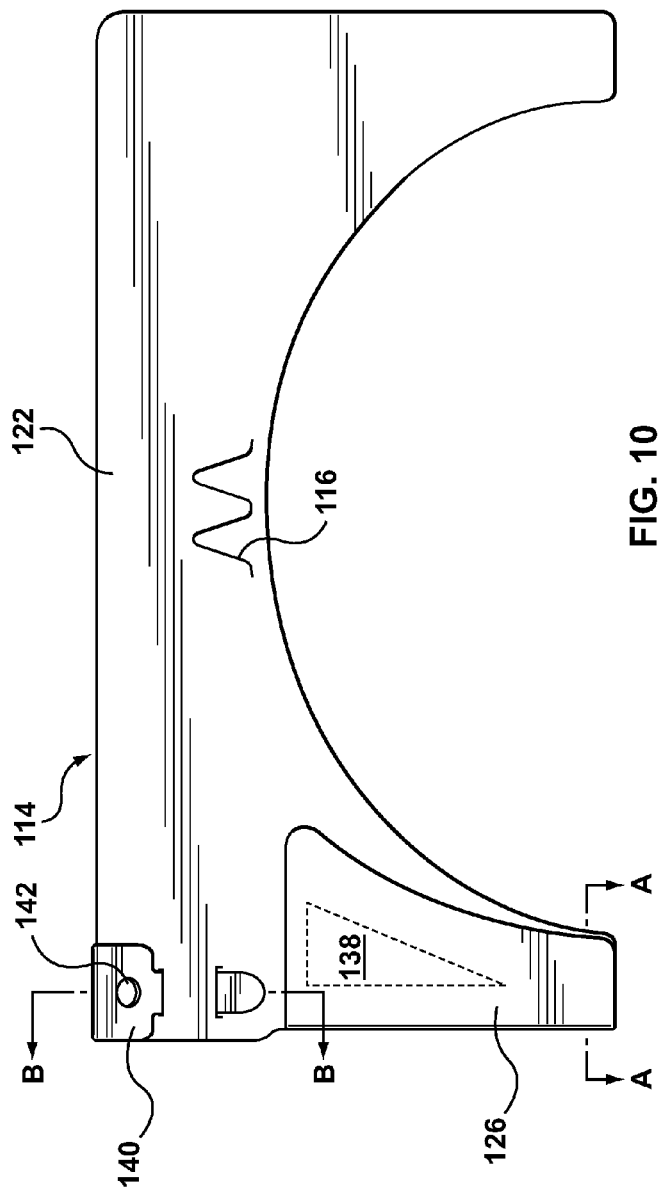

PACKAGING FOR A CATHETER

FIELD OF THE INVENTION

The present invention relates generally to catheters intended for deployment within a patient's vasculature, and more particularly, to packaging for a catheter.

BACKGROUND OF THE INVENTION

Catheters may be inserted into a patient's vasculature and deployed at various locations within the patient for a wide variety of purposes and medical procedures. For example, one type of catheter is used in percutaneous catheter intervention (PCI) for the treatment of a vascular constriction generally known as a stenosis. In this instance, the catheter has a distally mounted balloon that can be placed, in a deflated or collapsed condition, within the stenosis, and then inflated or expanded to dilate the narrowed lumen of a blood vessel. This type of balloon dilation therapy is generally referred to as percutaneous transluminal angioplasty (PTA). When the treatment is more specifically intended for vessels of the heart, the process is known as percutaneous transluminal coronary angioplasty (PTCA). PTCA is utilized to open coronary arteries that have been occluded by a buildup of cholesterol fats and atherosclerotic plaque. The balloon at the distal end of the catheter is inflated causing a widening at the site of the stenosis.

Dilation of an occlusion, however, can form flaps, fissures, and dissections, that may result in re-closure of the dilated vessel or even perforations in the vessel wall. Implantation of a stent or other prosthesis can provide support for such flaps and dissections and thereby prevent re-closure of the vessel or provide a patch repair for a perforated vessel wall until corrective surgery can be performed. The stent is typically a cylindrically shaped device formed from wire(s) or a metal tube and is intended to act as a permanent prosthesis. The stent is deployed in a body lumen in a radially compressed configuration and is subsequently radially expanded to contact and support a body lumen. The stent can be implanted during an angioplasty procedure by using a balloon catheter having deployed thereon a compressed stent that has been loaded onto the balloon. The stent radially expands as the balloon is inflated thus forcing the stent into contact with the body lumen and forming a supporting relationship with the lumen walls. Alternatively, self expanding stents may be deployed with a sheath-based delivery catheter. Deployment is effected after the stent has been introduced percutaneously, transported transluminally, and positioned at a desired location by the delivery catheter. In addition to angioplasty and stenting procedures, other therapeutic procedures require the use of a delivery catheter; e.g. drug delivery devices, filters, occlusion devices, diagnostic devices, and radiation treatment.

Catheters, including both over-the-wire catheters and rapid exchange catheters, are commonly packaged and stored in a packaging hoop that consists of coiled tubing into which the catheter is inserted. A luer fitting located at the proximal end of the catheter is provided with a distal hub that fits into an opening in the tubing thus securing the catheter in the hoop. Balloons and/or stents are commonly disposed on a distal portion of catheters. When removing the catheter from the packaging hoop, an operator may grasp the proximal end of the hoop in order to separate the luer fitting from the hoop. However, by grasping the proximal end of the hoop, the opening in the tubing may become misshapen due to pressure from the fingers of the operator. Accordingly, when the balloon and/or stent attempt to pass through the opening, one or both may become damaged. Such damage may be especially problematic with coated stents which are now popular.

Accordingly, an improved packaging arrangement is desirable that discourages grasping the packaging at a location that can potentially damage an object passing through the packaging, such as a balloon and/or stent.

BRIEF SUMMARY OF THE INVENTION

Embodiments hereof relate to a packaging device for a catheter having an elongated shaft and a proximal luer. The packaging device includes a coiled tube defining a lumen configured to receive the elongated shaft of the catheter, and a substantially planar mounting card coupled to the coiled tube. The mounting card includes an integral moveable luer retainer configured to selectively alternate between a first configuration which secures the proximal luer of the catheter within an opening formed on the luer retainer and a second configuration which releases the luer from the opening on the luer retainer and eases insertion and removal of the catheter. The mounting card may also include an integral support flap that folds over a proximal segment of the coiled tubing and creates a generally triangular contact zone to press when removing the elongated shaft of the catheter from the coiled tube. The mounting card may also include a sinusoidal cut which forms at least one integral tab for attaching an accessory bag thereto.

Embodiments hereof also relate to a method of inserting a catheter into a packaging device. A packaging device having a coiled tube defining a lumen is configured to receive an elongated shaft of the catheter and includes a substantially planar mounting card coupled to the coiled tube. The mounting card includes an integral moveable luer retainer configured to selectively alternate between a first configuration which secures the proximal luer of the catheter within an opening formed on the luer retainer and a second configuration which releases the proximal luer from the opening and eases insertion and removal of the catheter. A distal end of the catheter is inserted into a proximal opening of the coiled tubing. The catheter is threaded through the coiled tubing until a proximal luer of the catheter abuts against the proximal opening of the coiled tubing. The luer retainer is positioned in the second configuration to insert the proximal luer into the opening in the luer retainer and transitioned to the first configuration such that a proximal end of the proximal luer of the catheter is secured within the opening formed on the luer retainer.

Embodiments hereof also relate to a method of removing a catheter from a packaging device. The packaging device with a catheter secured therein includes a coiled tube which houses an elongated shaft of the catheter and a substantially planar mounting card coupled to the coiled tube. The mounting card includes an integral moveable luer retainer that in a first configuration secures a proximal luer of the catheter within an opening formed on the luer retainer. The luer retainer of the mounting card is transformed from the first configuration into a second configuration which releases the proximal luer from the luer retainer. The proximal luer of the catheter is grasped and the catheter is removed by pulling on the catheter until its distal end is released from the coiled tubing. The step of removing the catheter is performed while simultaneously grasping a contact zone created by an integral support flap of the mounting card that folds over a proximal segment of the coiled tubing.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 8 is a top view illustration of the catheter packaging of FIG. 5 without a catheter secured therein.

FIG. 9 is a top view illustration of the welded coiled tubing of the catheter packaging illustrated in FIG. 8.

FIG. 10 is a top view illustration of the mounting card of the catheter packaging illustrated in FIG. 8.

FIG. 10A is a cross-sectional view taken along line A-A of FIG. 10.

FIG. 10B is a cross-sectional view taken along line B-B of FIG. 10, wherein the luer retainer is positioned in a first configuration which secures the proximal luer of the catheter.

FIG. 10C is a cross-sectional view taken along line B-B of FIG. 10, wherein the luer retainer is positioned in a second configuration which releases the proximal luer from the luer retainer and eases insertion and removal of the catheter.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figures 1, 2:
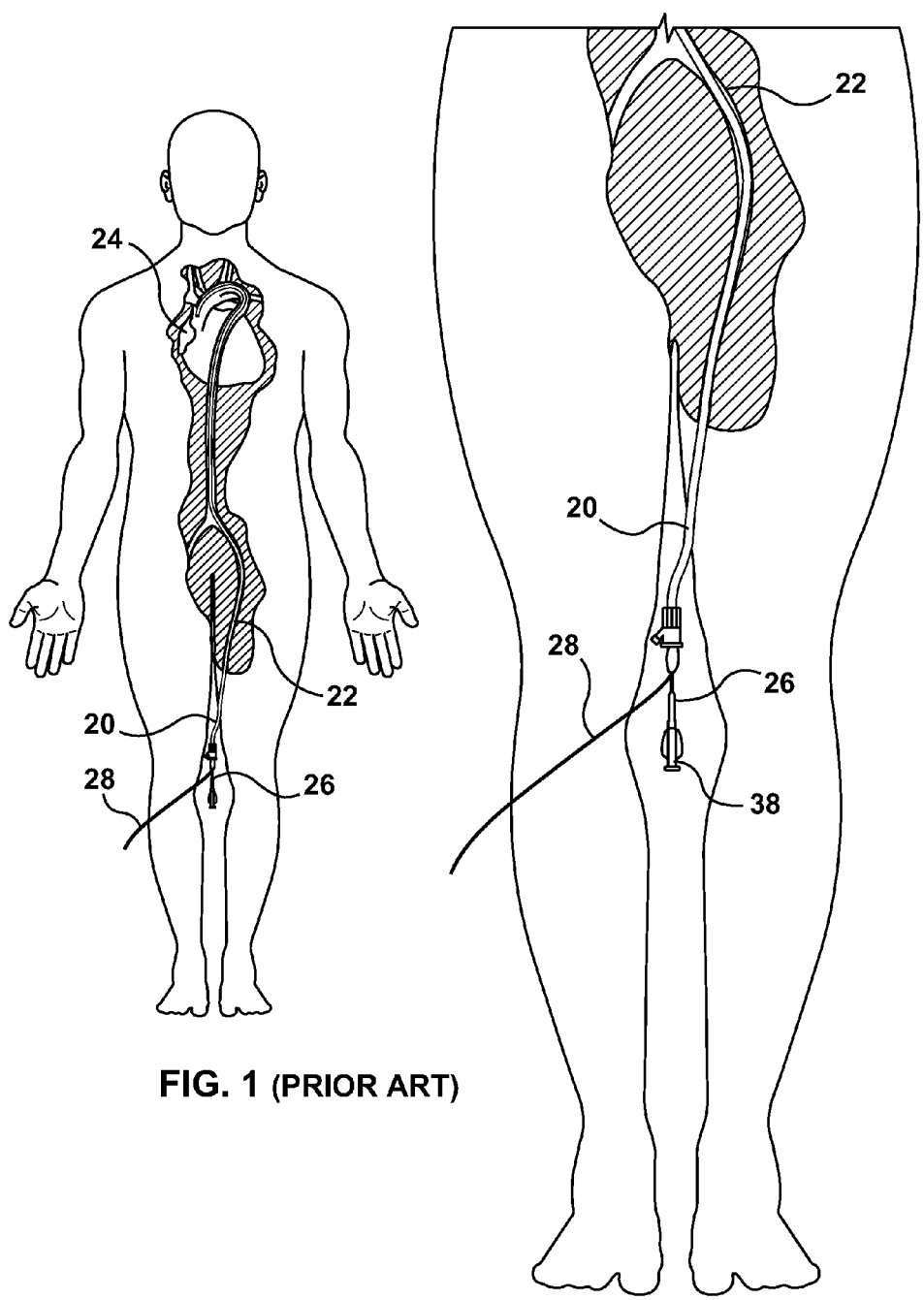
FIG. 1 is a diagrammatic drawing illustrating the deployment of a balloon catheter within a patient's vasculature.
FIG. 2 is an enlarged diagrammatic drawing of a portion of FIG. 1.

As stated previously, to treat small diameter vessels remote from an entry point into a patient, a guiding catheter may be used to span the distance. For example, FIGS. 1 and 2 illustrate the deployment of a balloon catheter within a patient's vasculature. In PTCA or stent delivery, a guiding catheter 20 is typically inserted into a large artery 22 near the patient's groin and is then advanced towards heart 24 to the entry opening or ostium of a diseased coronary artery. Guiding catheter 20 provides a conduit through which catheters and guide wires, such as a treatment catheter 26 and a guide wire 28, can be passed from outside the patient to the vessel being treated. As known by those of ordinary skill in the art, treatment catheter 26 generally includes a distal flexible elongated shaft and a proximal luer fitting 38.

Figures 3, 4:
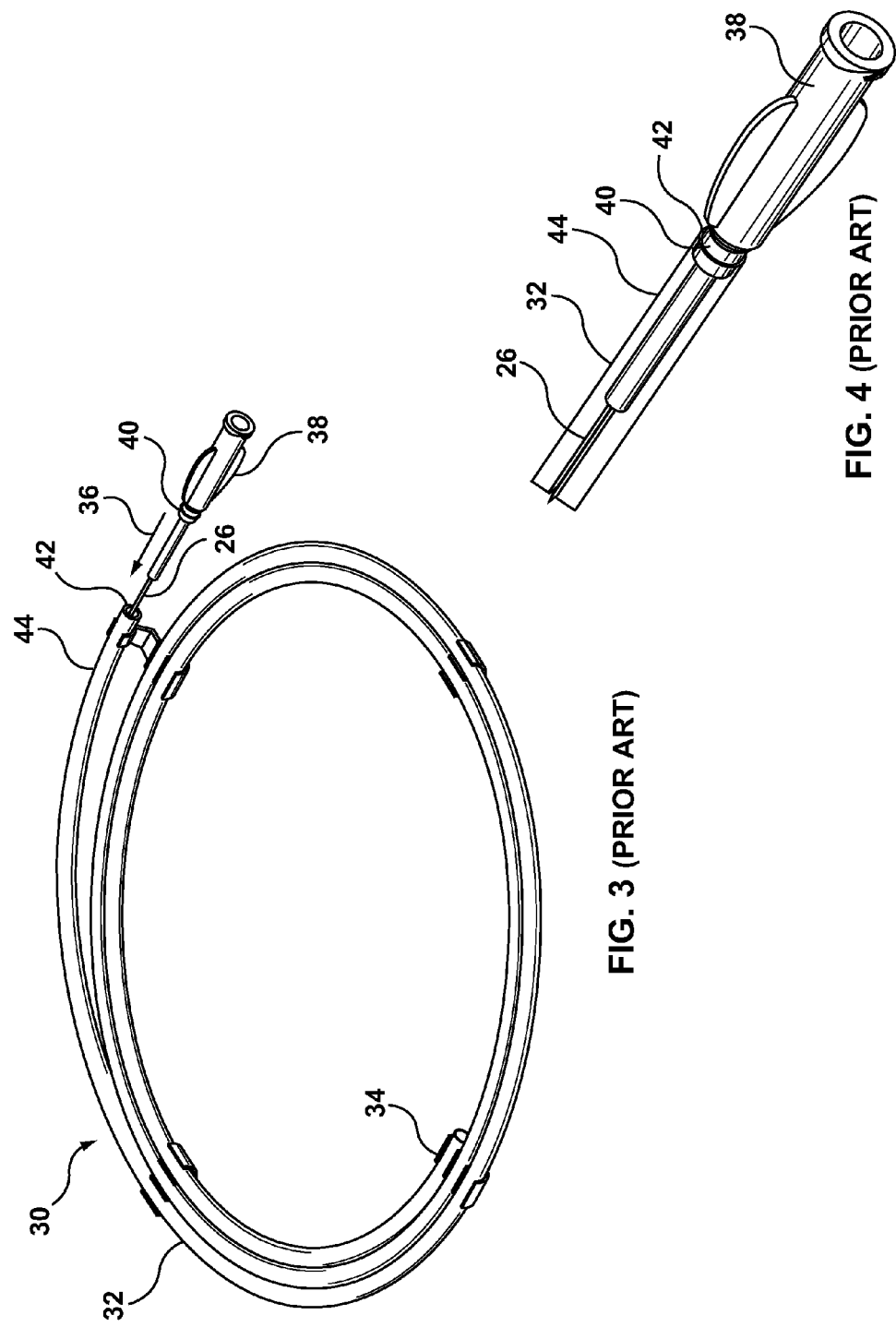
FIG. 3 illustrates a conventional catheter packaging hoop with a catheter partially inserted into the hoop.
FIG. 4 illustrates the conventional catheter packaging hoop of FIG. 3 with the catheter fully inserted into the hoop.

Referring now to FIGS. 3-4, catheters are commonly packaged and stored in a packaging hoop 30 as shown in FIG. 3 in accordance with the teachings of the prior art. Packaging hoop 30 consists of coiled tubing 32 into which treatment catheter 26 is inserted in the direction indicated by arrow 36. Clips 34 are coupled to tubing 32 to maintain the tubing 32 in the coiled configuration. Luer fitting 38, located at the proximal end of treatment catheter 26, has a distal hub 40 that fits into proximal opening 42 of tubing 32, thus securing treatment catheter 26 in hoop 30 as is shown in FIG. 4. However, as discussed above, treatment catheter 26 generally includes a balloon (not shown) disposed at a distal portion thereof and/or a stent (not shown). When removing treatment catheter 26 from packaging hoop 30, it is common for an operator to grasp luer 38 with one hand, grasp a proximal portion 44 of tubing 32 in the other hand, and pull luer 38 away from tubing 32. However, when grasping proximal portion 44 of tubing 32, pressure may be applied to tubing 32 which causes opening 42 to lose its shape. As treatment catheter 26 continues to be removed from tubing 32, the balloon and/or stent need to pass through opening 42. However, as opening 42 may be misshapen as described above, the balloon and/or stent may be damaged upon removal.

Figure 5:
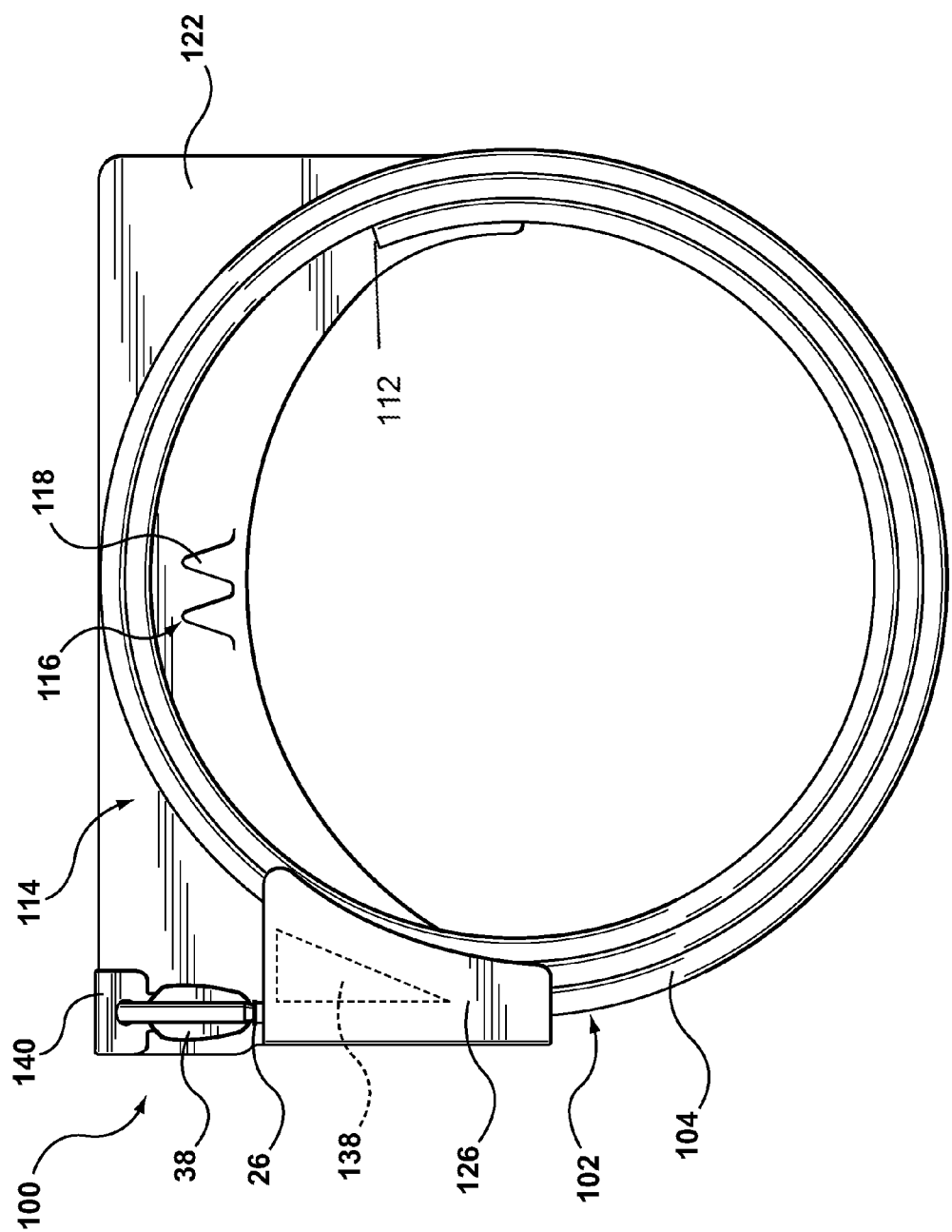
FIG. 5 is a top view illustration of catheter packaging according to an embodiment of the present invention, wherein a catheter is fully secured within the packaging.

Turning now to FIG. 5, an embodiment of catheter packaging 100 according to the present invention is shown. As will be explained herein, packaging 100 discourages grasping the packaging at a location that can potentially damage an object passing through the packaging, such as a balloon and/or stent. In addition, as explained herein, packaging 100 also includes an integral moveable luer retainer which secures the proximal luer of a catheter but also allows for easy removal and insertion of the catheter into the packaging. In FIG. 5, treatment catheter 26 is fully secured within packaging 100 while FIG. 8 illustrates packaging 100 without a catheter secured therein. Packaging 100 includes two main components, coiled tubing 102 for receiving the elongated shaft of catheter 26 and a mounting card 114 which, among other features, may include an integral luer retainer 140 for securing luer 38 of catheter 26, an integral support flap 126 creating a contact zone 138, and integral tabs 118 for attaching an accessory bag thereto.

Turning to FIG. 9, tubing 102 is shown removed or separated from mounting card 114 for illustrative purposes only. Tubing 102 extends from a proximal opening 110 to a distal opening 112 and defines a lumen 103 for receiving catheter 26. Tubing 102 is coiled into multiple adjacent loops or windings 104. With the exception of a proximal segment 108 of tubing 102, adjacent windings 104 are continuously coupled together via a bond, adhesive, or weld 106 to maintain tubing 102 in the coiled configuration.

Proximal segment 108 of tubing 102 extends away from and is detached from adjacent windings 104.

Referring to FIG. 8 showing packaging 100 without a catheter inserted therein, at least a portion of tubing 102 is coupled to mounting card 114. At least a portion of coiled tubing 102 lays flat on a planar surface of mounting card 114 with adjacent windings 104 abutting against the mounting card 114. In one embodiment, only proximal segment 108 of tubing 102 and a segment of tubing 102 adjacent to distal opening 112 are coupled to mounting card 114 via a bond, adhesive, or weld. The attachment between proximal and distal segments of tubing to mounting card 114 ensures that coiled tubing 102 is secure and stable on mounting card 114 while minimizing the required materials and size of packaging 100. It would be understood by those of ordinary skill in the art that in other embodiments, more portions of tubing 102 which contact mounting card 114 may be coupled to mounting card 114 via a bond, adhesive, or weld, up to and including all portions of tubing which contact mounting card 114 being coupled to mounting card 114 via a bond, adhesive or weld. In addition, it would be understood by those of ordinary skill in the art that mounting card 114 is not limited to the rectangular configuration shown in the figures but may also have a square configuration in which the all of coiled tubing 102 lays flat on a planar surface of mounting card 114 and may be coupled thereto via a bond, adhesive, or weld.

Figure 11:
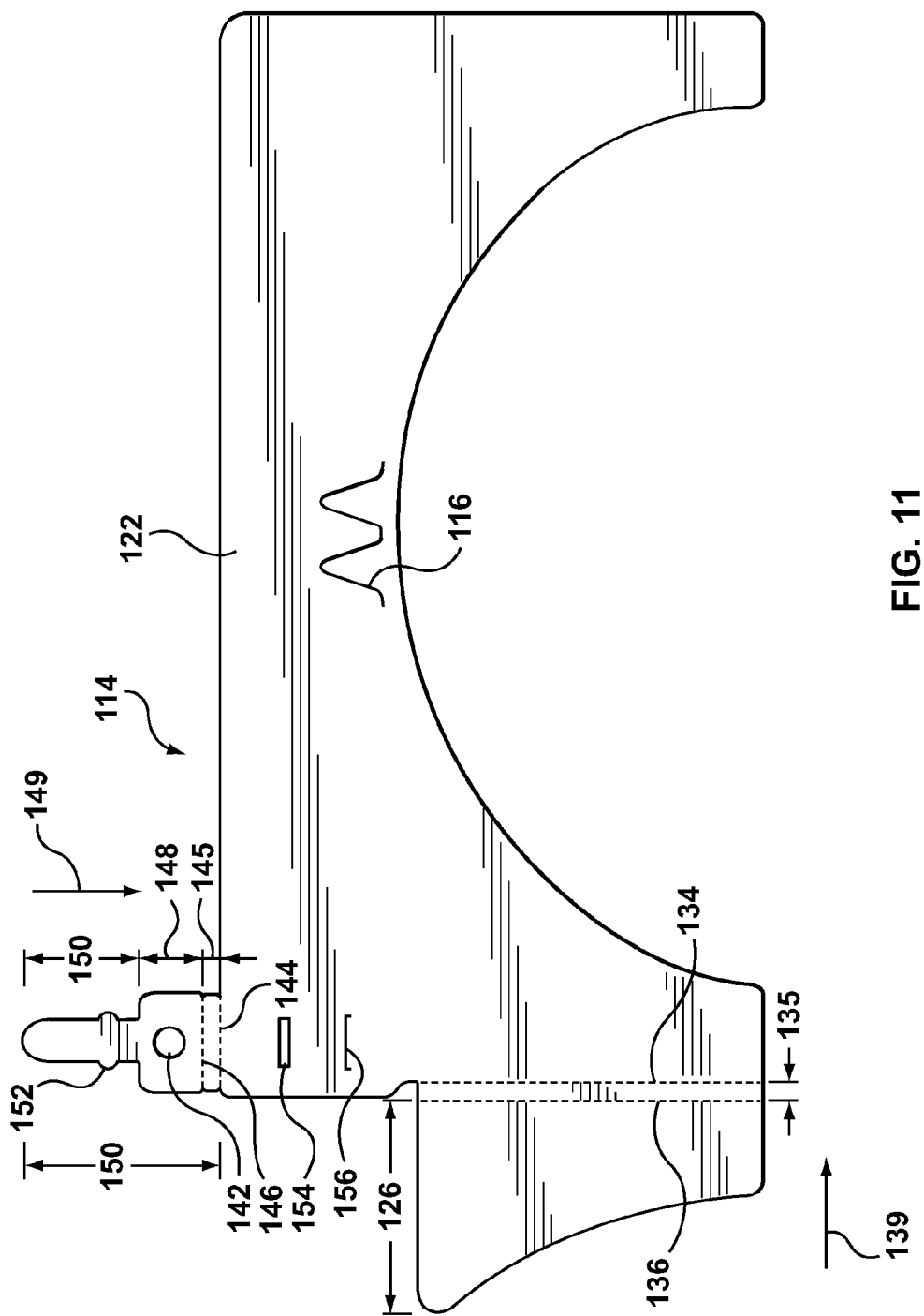
FIG. 11 is a top view illustration of the mounting card of the catheter packaging illustrated in FIG. 8, wherein an integral support flap of the mounting card which forms a contact zone for catheter removal and the luer retainer of the mounting card are laid flat for illustrative purposes only.

Mounting card 114 is a single continuous component that has several features. Mounting card 114 includes an integral support flap 126 for reducing the risk of damage to tubing 102 during catheter insertion or removal, integral luer retainer 140 for securing a catheter luer, and one or more integral tabs 118 for attaching catheter accessories to packaging 100. As best shown in FIG. 11 in which integral support flap 126 and integral luer retainer 140 are laid out flat for illustrative purposes only, mounting card 114 is described as having three continuous sections including integral support flap 126, integral luer retainer 140, and a backing 122. Backing 122 is a generally planar piece of material and is intended to represent all material of mounting card 114 except for flap 126 and luer retainer 140 which both extend from backing 122.

Figure 6:
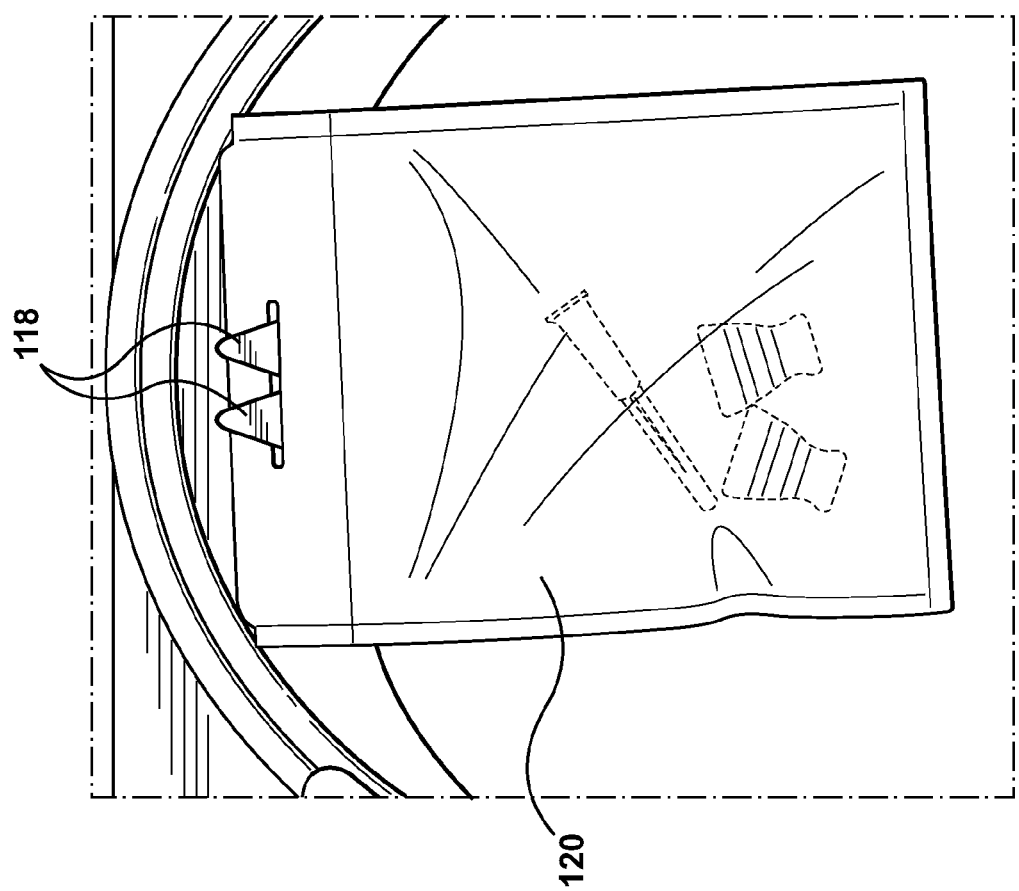
FIG. 6 is a top view illustration of a portion of the catheter packaging of FIG. 5, wherein an accessory bag is removably coupled to the catheter packaging.

Referring to FIG. 10 and FIG. 6, mounting card 114 includes a sinusoidal cut or slit 116 formed through backing 122. Slit 116 forms one or more integral tabs 118 for attaching an accessory bag 120 to packaging 100. Accessory bag 120 may house various components such as but not limited to a cannula, a wire insertion, a looper used to clip the catheter after it is taken out of coiled tubing 102, a desiccant and oxygen scavenger, and/or instructions for use that may be utilized with packaging 100 and/or catheter 26. In the embodiment depicted in FIG. 6 and FIG. 10, packaging 100 includes two tabs 118 but it will be understood by those of ordinary skill in the art that slit 116 may form only one tab or may form more than two tabs.

Another feature of mounting card 114 is integral support flap 126 that covers a portion of coiled tubing 102 and creates a generally triangular contact zone 138 for the operator to grasp during insertion or removal of catheter 26 from packaging 100. More particularly, when removing catheter 26 from packaging 100, an operator may grasp luer 38 of catheter 26 with one hand, grasp mounting card 114 on contact zone 138 of integral support flap 126 in the other hand, and pull the elongated shaft of catheter 26 out of tubing 102. By applying pressure to contact zone 138, little or no pressure is applied to proximal portion 108 of tubing 102 and therefore proximal opening 110 does not lose its shape. Accordingly, the balloon and/or stent of catheter 26 may safely pass through proximal opening 110 of packaging 100 without damage thereto. The operator may similarly grasp mounting card 114 on contact zone 138 in one hand while inserting the elongated shaft of catheter 126 into tubing 102 and pushing the elongated shaft of catheter 126 through tubing 102 with the other hand.

Integral support flap 126 is further described with respect to FIG. 10, FIG. 10A, and FIG. 11. In FIG. 11, flap 126 is laid out flat for illustrative purposes only. However, in use, flap 126 folds over backing 122 of mounting card 114 as shown in the top view of FIG. 10 and the cross-sectional view of FIG. 10A. An edge 136 which is represented as a perforated line separates flap 126 from a connector segment 135, and an edge 134 which is also represented as a perforated line separates connector segment 135 and backing 122. Flap 126 is formed by folding edges 134, 136 in a direction represented by arrow 139 (see FIG. 11) such that connector segment 135 extends in a perpendicular direction to flap 126 and backing 122 (see FIG. 10A). Flap 126 and backing 122 extend generally parallel to each other and define a slot or recess 132 for receiving coiled tubing 102. Although described as separate component, flap 126, connector segment 135, and backing 122 are formed from a continuous integral piece of material forming mounting card 114. Integral support flap 126 may further include a second connector segment (not shown) opposite connector segment 135 shown in FIG. 10A that may be welded or otherwise connected to backing 122 and/or support flap 126 to provide further support for contact zone 138.

Figure 7:
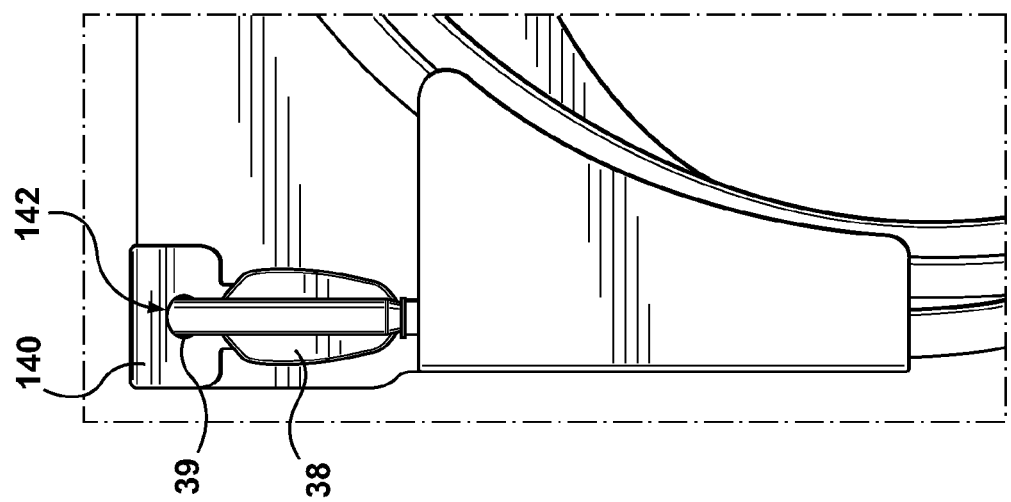
FIG. 7 is an enlarged illustration of a portion of the catheter packaging of FIG. 5 showing the luer of the catheter secured within the catheter packaging.

Mounting card 114 may also include an integral luer retainer 140 for removably securing luer 38 of catheter 26. As shown in FIG. 7, a proximal end 39 of luer 38 is secured within an opening 142 of luer retainer 140. When luer 38 of catheter 26 is secured within packaging 100, it is protected from undesired movement and potential damage during transport and storage.

Luer retainer 140 is further described with respect to FIG. 10, FIG. 10B, 10C, and FIG. 11. In FIG. 11, luer retainer 140 is laid out flat for illustrative purposes only. However, in use, luer retainer 140 folds over backing 122 of mounting card 114 as shown in the top view of FIG. 10 and the sectional view of FIG. 10B. Luer retainer 140 is essentially an elongated tab extending from backing 122 of mounting card 114. For illustrative purposes, luer retainer 140 may be considered as having three sections, although it should be understood that luer retainer 140 is a portion of a continuous integral piece of material forming mounting card 114. Luer retainer 140 includes a connector segment 145, a platform 148 having opening 142 formed therein, and an elongated tongue 150. An edge 144 which is represented as a perforated line separates connector segment 145 and backing 122 of mounting card 114, and an edge 146 which is also represented as a perforated line separates connector segment 145 and platform 148. Luer retainer 140 is formed by folding edges 144, 146 toward a front surface of backing 122, as represented by arrow 149 (see FIG. 11) such that connector segment 145 extends in a direction generally perpendicular to backing 122 (see FIG. 10A). Platform 128 extends at an acute angle relative to connector segment 145 to an opening or slot 154 formed in backing 122 of mounting card 114. Tongue 150 slidingly extends in a downward direction through backing 122 via slot 154 as shown in FIG. 10B. In one embodiment, the unattached end of tongue 150 is further threaded in an upwards direction through a slit 156 formed in backing 122 of mounting card 114 to tightly secure the unattached end of tongue 150. In one embodiment, slit 156 may be generally U-shaped to form a small flap or tab 158 that exerts an upward force onto tongue 150 to tightly secure the unattached end of tongue 150 into slit 156 as shown in FIG. 10B.

Luer retainer 140 is configured to selectively alternate between a first configuration which secures the proximal luer of the catheter shown in FIG. 10B and a second configuration which releases the luer from the luer retainer and eases insertion and removal of the catheter shown in FIG. 10C. More particularly, when luer retainer 140 is in the first configuration which secures the proximal luer of the catheter shown in FIG. 10B, connector segment 145 of luer retainer 140 is generally perpendicular to backing 122 such that platform 148 having hole 142 thereon is properly positioned to receive the proximal end of a catheter luer. In addition, tongue 150 may include lateral protrusions 152 (see FIG. 11) such that when luer retainer 140 is in the first configuration which secures the proximal luer of the catheter, lateral protrusions 152 are positioned along a back surface of backing 122 (opposite the top surface to which tubing 102 is attached), between slot 154 and slit 156. Lateral protrusions 152 are slightly wider in dimension than slot 154 so that once they are positioned underneath backing 122, they function as a stop to retain luer retainer 140 into place in the first configuration which secures the proximal luer of the catheter.

When it is desired to insert or release a catheter into packaging 100, luer retainer 140 may be selectively transformed into the second configuration which releases the luer from the luer retainer and eases insertion and removal of the catheter shown in FIG. 10C. More particularly, when luer retainer 140 is in the second configuration shown in FIG. 10C, connector segment 145 of luer retainer 140 is moved to extend at an obtuse angle relative to backing 122. The obtuse angle may be any angle between 90° and 180°, but in one embodiment the obtuse angle is approximately 135°. As a result of reclining connector segment 145, platform 148 also reclines and moves away from the location in which it functions to secure the proximal end of the catheter luer. Lastly, as a result of the applied force to recline connector segment 145, lateral protrusions 152 on tongue 150 may pass through slot 154 on backing 122 such that protrusions 152 are located along a top surface of backing 122. With lateral protrusions 152 located along the top surface of backing 122, luer retainer 140 is not locked in place but rather can be reclined as needed to allow a catheter to be inserted into or removed from packaging 100.

Packaging 100, including both coiled tubing 102 and mounting card 114, are formed from any suitable material. Coiled tubing 102 may be formed from the same material as mounting card 114, or the components may be formed from different materials. In one embodiment, coiled tubing 102 and/or mounting card 114 are formed from polyethylene. In another embodiment, coiled tubing 102 and/or mounting card 114 are formed out of a recyclable material.

Figure 12:
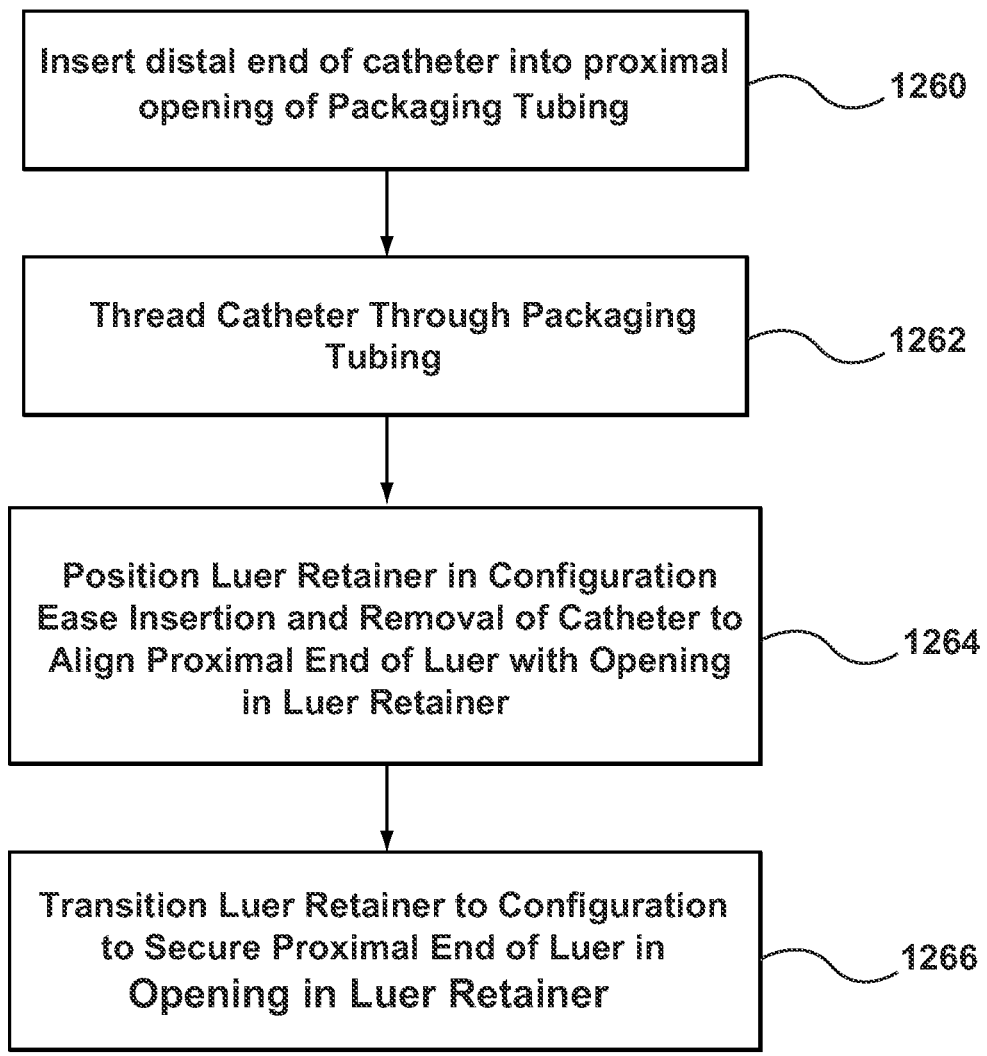
FIG. 12 is a flow chart illustrating a method of catheter insertion into the catheter packaging of FIG. 8.

Referring now to FIG. 12, a method of inserting a catheter into packaging 100 is described. In step 1260, luer retainer 140 is positioned into the configuration for securing the proximal luer, that is, the position of FIG. 10B. A distal end of a catheter is inserted into proximal opening 110 of tubing 102 as shown in step 1260 and the catheter is threaded through tubing 102 as indicated in step 1262 until the catheter luer abuts against proximal opening 110. The operator may grasp contact zone 138 during insertion of the distal end of the catheter into proximal opening 110 and threading of the catheter through tubing 102. Platform 148 is then pushed in a direction away from tubing 102 such that luer retainer 140 is transitioned to the configuration shown in FIG. 10C such that a proximal end of the luer may be aligned with opening 142 of luer retainer 140, as indicated in step 1264. Luer retainer 140 is then transitioned into the configuration which secures the proximal luer of the catheter described herein with respect to FIG. 10B and as indicated in step 1266. With the proximal end of the catheter luer securely positioned within hole 142 of luer retainer 140 (see FIG. 7), the catheter is secured within packaging 100 for transport and/or storage.

Figure 13:
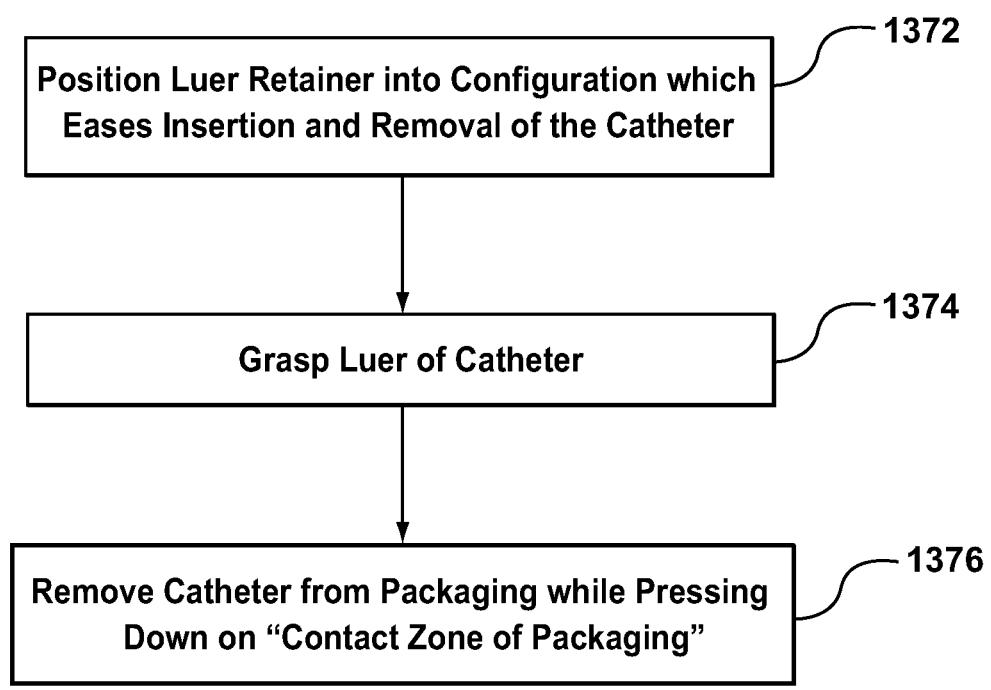
FIG. 13 is a flow chart illustrating a method of catheter removal from the catheter packaging of FIG. 8.

Referring now to FIG. 13, a method of removing a catheter from packaging 100 is described. In step 1372, an operator positions luer retainer 140 into the configuration which releases the proximal end of the luer of the catheter as described herein with respect to FIG. 10C. In one embodiment, while transitioning the configuration of the luer retainer, the operator simultaneously presses down on contact zone 138 of support flap 126. By grasping contact zone 138 while transitioning the luer retainer configuration, the pressure exerted by the operator ensures that the catheter retained within the packaging does not move with luer retainer 140 when the luer retainer is reclined into the configuration which eases insertion and removal of the catheter. In another embodiment, luer retainer 140 may be transitioned into the configuration which releases the proximal end of the luer without pressing down on contact zone 138. With luer retainer 140 positioned in the configuration which releases the proximal end of the luer, the catheter luer is released and free to be grasped by the operator as shown in step 1374. The operator may then remove the catheter from packaging 100 by pulling on the catheter until its distal end is released from tubing 102 of the packaging, as indicated by step 1376. During the removal step 1376, the operator should simultaneously grasp on contact zone 138 of support flap 126. For example, an operator may grasp the catheter luer with one hand, grasp mounting card 114 on contact zone 138 in the other hand, and pull the catheter out of tubing 102. By applying pressure to contact zone 138, little or no pressure is applied to proximal portion 108 of tubing 102 and therefore proximal opening 110 does not lose its shape. Accordingly, the balloon and/or stent of the catheter may safely pass through proximal opening 110 of packaging 100 without damage thereto.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A packaging device for a catheter having an elongated shaft and a proximal luer, the packaging device comprising:
   a coiled tube defining a lumen configured to receive the elongated shaft of the catheter, wherein adjacent windings of the coiled tube are welded together to maintain the tubing in the coiled configuration; and
   a substantially planar mounting card coupled to the coiled tube, wherein the mounting card includes an integral moveable luer retainer configured to selectively alternate between a first configuration which secures the proximal luer of the catheter within an opening formed on the luer retainer and a second configuration which releases the proximal luer of the catheter to ease insertion and removal of the catheter, wherein the mounting card further includes an integral support flap extending from the mounting card and extending over a proximal segment of the coiled tubing, wherein the luer retainer comprises an elongated tab extending from a backing of the mounting card and the luer retainer folds over and is threaded through at least one opening formed within the backing of the mounting card, and wherein a portion of the luer retainer extends approximately perpendicular to the backing of the mounting card when the luer retainer is in the first configuration and wherein the luer retainer reclines to form an obtuse angle with the backing of the mounting card when the luer retainer is in the second configuration.

2. The packaging device of claim 1, wherein mounting card is bonded, welded, or adhesively coupled to the coiled tube.

3. The packaging device of claim 1, wherein adjacent windings of the coiled tube are continuously welded together except for a proximal segment of the coiled tube which extends away from and is detached from the adjacent windings.

4. The packaging device of claim 1, wherein only a proximal segment of the coiled tube and a distal segment of the coiled tube are coupled to the mounting card.

5. The packaging device of claim 1, wherein the mounting card includes a sinusoidal cut which forms at least one integral tab for attaching an accessory bag thereto.

6. The packaging device of claim 1, wherein the luer retainer includes at least one lateral protrusion that is a wider dimension than the at least one opening formed within the backing of the mounting card and wherein the at least one lateral protrusion is threaded through the at least one opening formed within the backing of the mounting card to retain the luer retainer in place when the luer retainer is in the first configuration.

7. A packaging device for a catheter having an elongated shaft, the packaging device comprising:

a coiled tube defining a lumen configured to receive the elongated shaft of the catheter, wherein adjacent windings of the coiled tube are welded together to maintain the tubing in the coiled configuration, wherein the coiled tubing includes a proximal segment that is not attached to an adjacent winding such that a gap is disposed between the proximal segment and the adjacent winding; and a substantially planar mounting card coupled to the coiled tube, wherein the mounting card includes an integral support flap that extends from the mounting card adjacent a first side of the proximal segment of the coiled tubing, folds over a second side of the proximal segment of the coiled tubing opposite the first side, and extends across the gap to the adjacent winding such that a space is disposed between the mounting card and the support flap at the gap such that contact zone is created by the integral support flap between the proximal segment and the adjacent winding.

8. The packaging device of claim 7, wherein the contact zone is configured to be pressed when inserting or removing the elongated shaft of the catheter from the coiled tube such that when the contact zone is pressed the proximal segment is not deformed.

9. The packaging device of claim 7, wherein mounting card is bonded, welded, or adhesively coupled to the coiled tube.

10. The packaging device of claim 7, wherein the mounting card includes a sinusoidal cut which forms at least one integral tab for attaching an accessory bag thereto.

11. The packaging device of claim 7, further comprising a luer retainer integral with the mounting card, the luer retainer being selectively moveable between a first configuration which secures a proximal luer of the catheter within an opening formed on the luer retainer and a second configuration which releases the proximal luer of the catheter to ease insertion and removal of the catheter.

12. The packaging device of claim 11, wherein the luer retainer comprises an elongated tab extending from a backing of the mounting card and the luer retainer folds over and is threaded through at least one opening formed within the backing of the mounting card.

13. The packaging device of claim 12, wherein a portion of the luer retainer extends approximately perpendicular to the backing of the mounting card when the luer retainer is in the first configuration and wherein the luer retainer reclines to form an obtuse angle with the backing of the mounting card when the luer retainer is in the second configuration.

* * * * *